United States Patent [19]

Kusenberger et al.

[11] Patent Number: 4,573,013

[45] Date of Patent: Feb. 25, 1986

[54] MAGNETIC INSPECTION OF REINFORCING STEEL RODS IN PRESTRESSED CONCRETE

[75] Inventors: Felix N. Kusenberger, San Antonio; John R. Barton, Bulverde; George A. Ferguson, San Antonio, all of Tex.

[73] Assignee: The United States of America as represented by the Secretary of Transportation, Washington, D.C.

[21] Appl. No.: 363,343

[22] Filed: Mar. 29, 1982

[51] Int. Cl.[4] .................... G01N 27/82; G01R 33/12
[52] U.S. Cl. .................................... 324/238; 324/235
[58] Field of Search ............. 324/251, 235, 238, 239, 324/240, 262, 228, 226, 241, 242, 243

[56] References Cited

U.S. PATENT DOCUMENTS

| | | | |
|---|---|---|---|
| 3,340,467 | 9/1967 | In Whan Ha | 324/228 |
| 3,811,320 | 5/1974 | Cowell | 324/262 X |
| 4,096,437 | 6/1978 | Kitzinger | 324/235 |
| 4,270,088 | 5/1981 | Weischedel | 324/242 |
| 4,270,089 | 5/1981 | Huberlein | 324/262 |

FOREIGN PATENT DOCUMENTS 557312  6/1977  U.S.S.R. ............................. 324/227

Primary Examiner—Reinhard J. Eisenzopf
Assistant Examiner—Walter E. Snow
Attorney, Agent, or Firm—Otto M. Wildensteiner; Harold P. Deeley, Jr.

[57] ABSTRACT

A method of inspecting the reinforcing members in prestressed concrete beams by generating a magnetic field close to the beam and measuring the field by means of a Hall effect sensor located between the pole pieces of the magnet. A partial or total break in a reinforcing member produces an anomaly in the magnetic field, which in turn registers as a voltage "spike" in the output of the Hall effect sensor. The method further includes a method for enhancing the data by substantially reducing or eliminating the effects of transverse reinforcing steel or support members located at the site of a break in the prestressed member.

1 Claim, 15 Drawing Figures

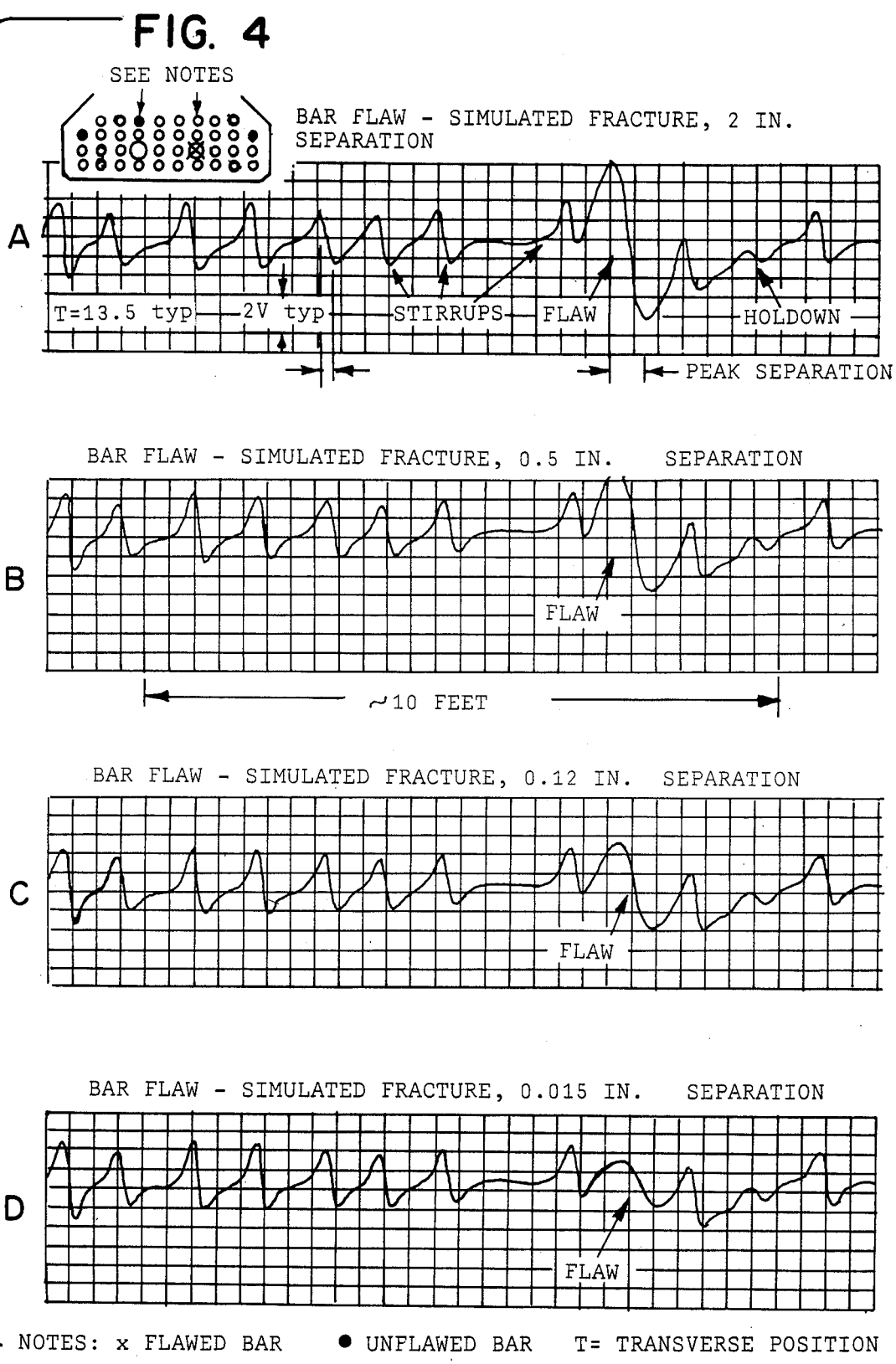

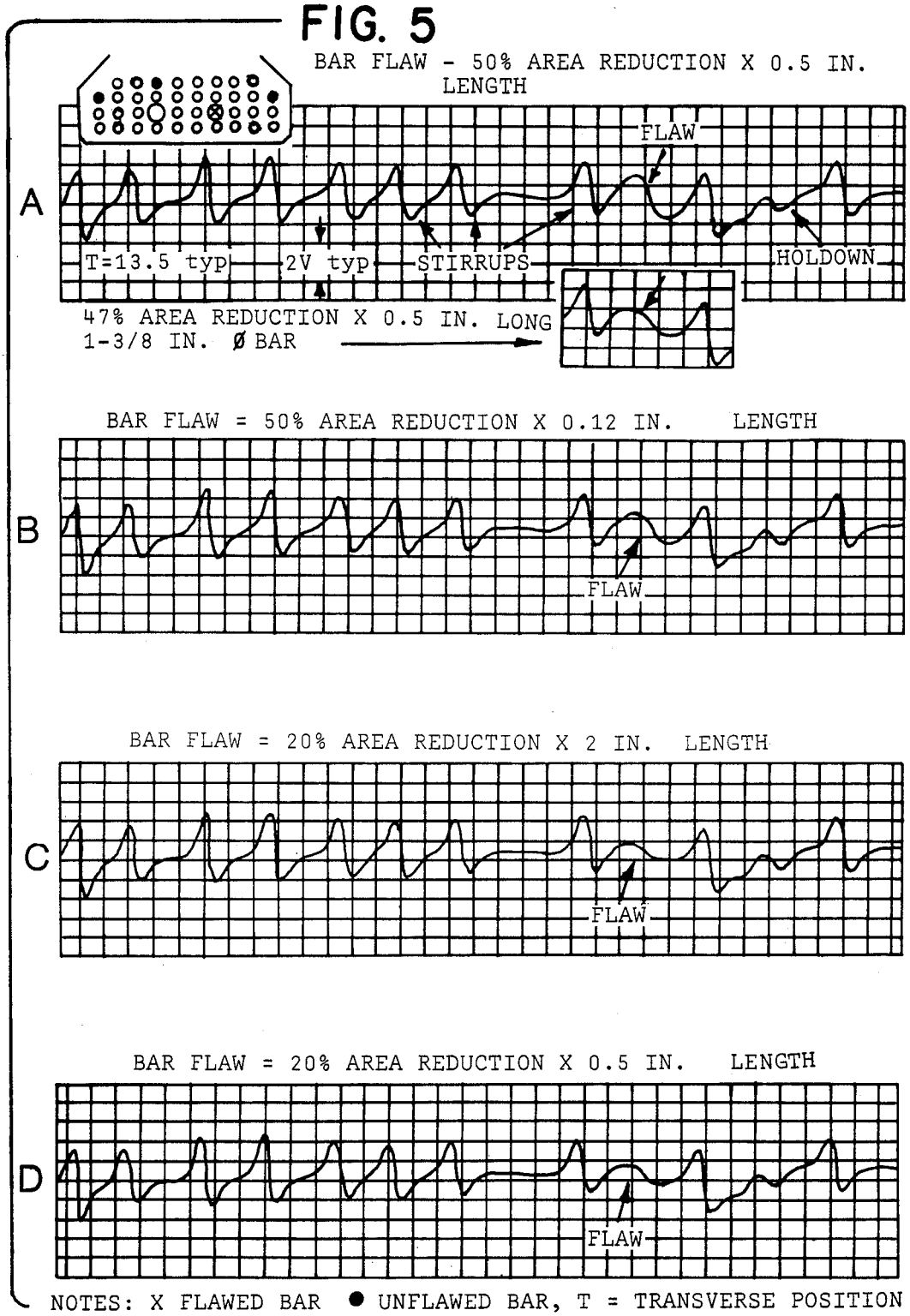

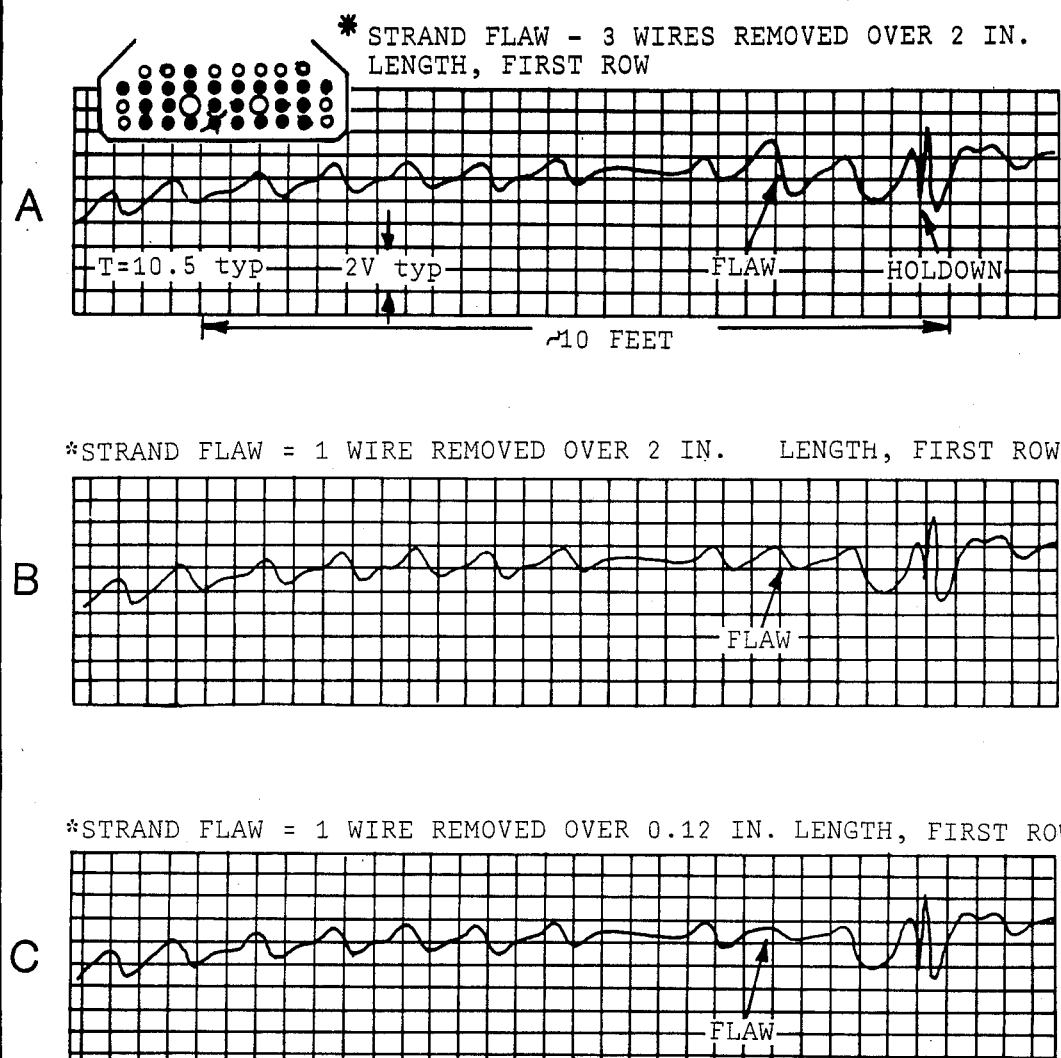

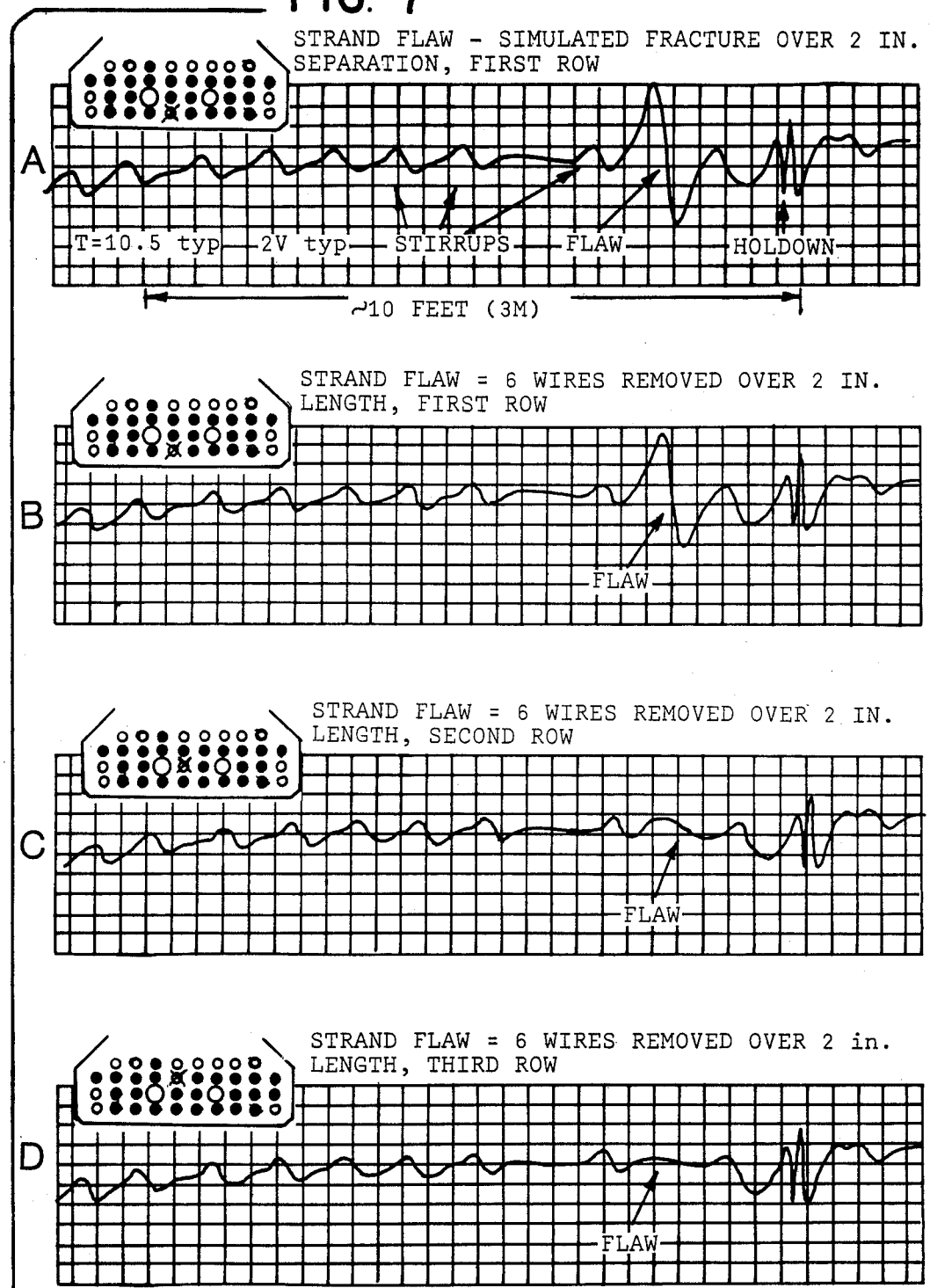

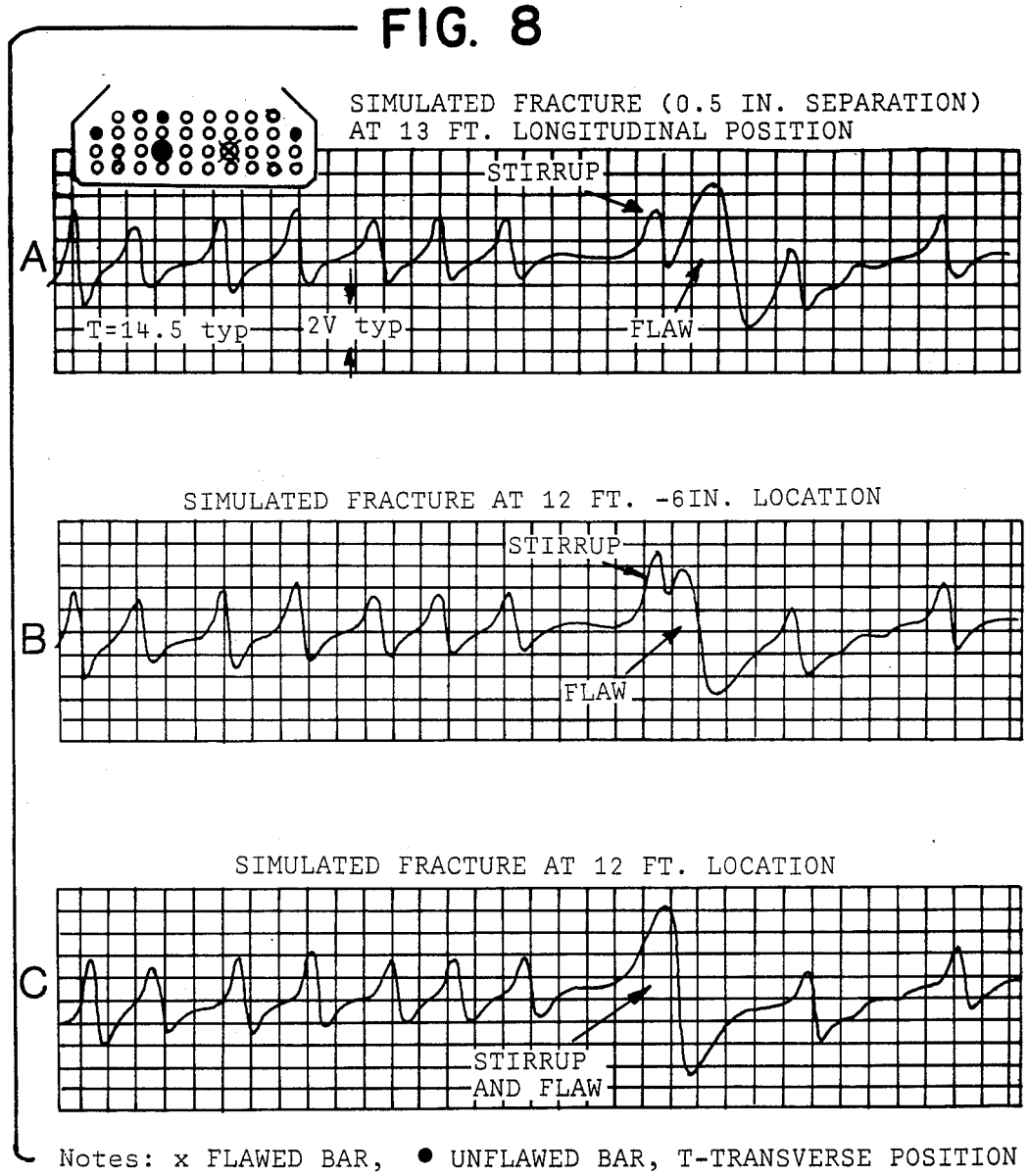

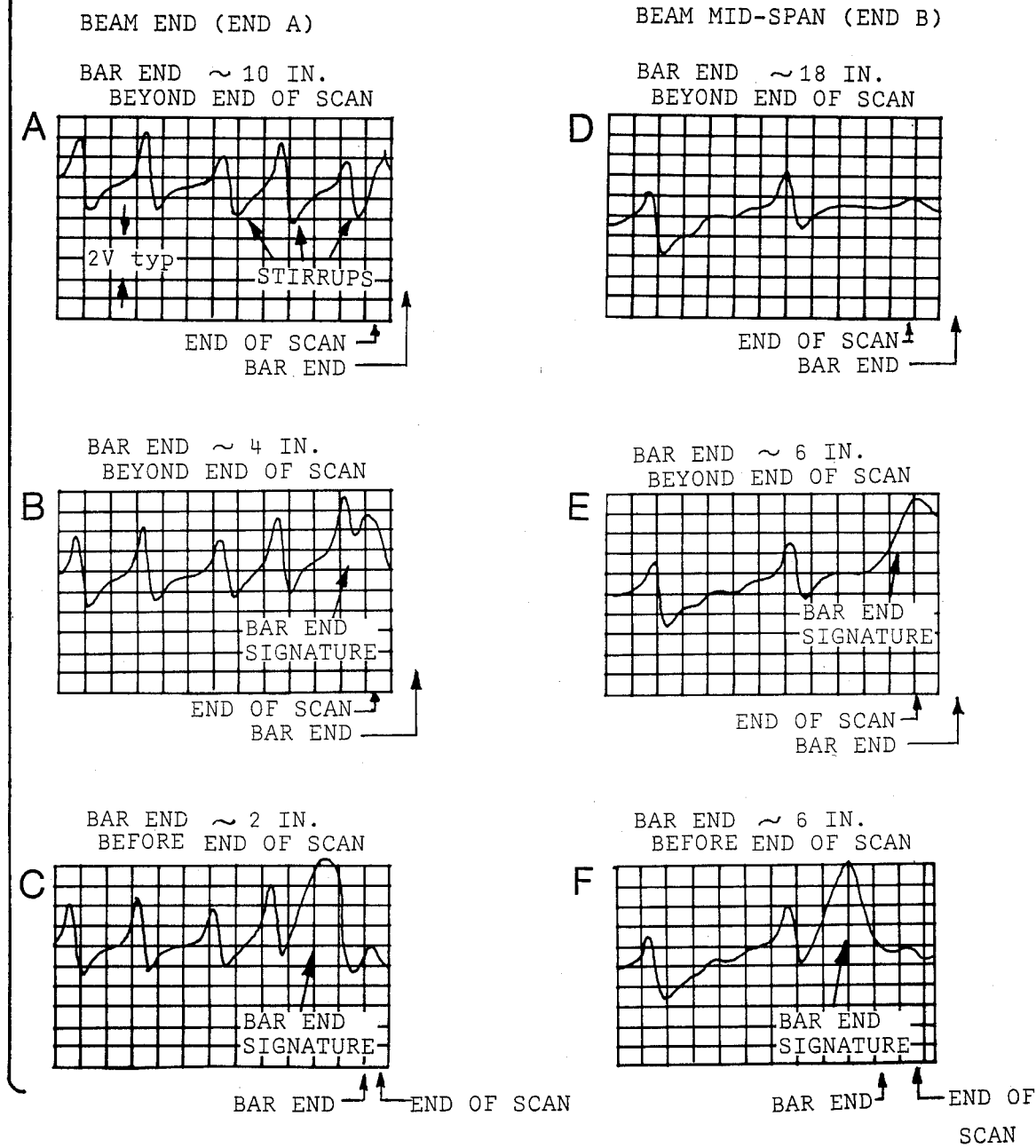

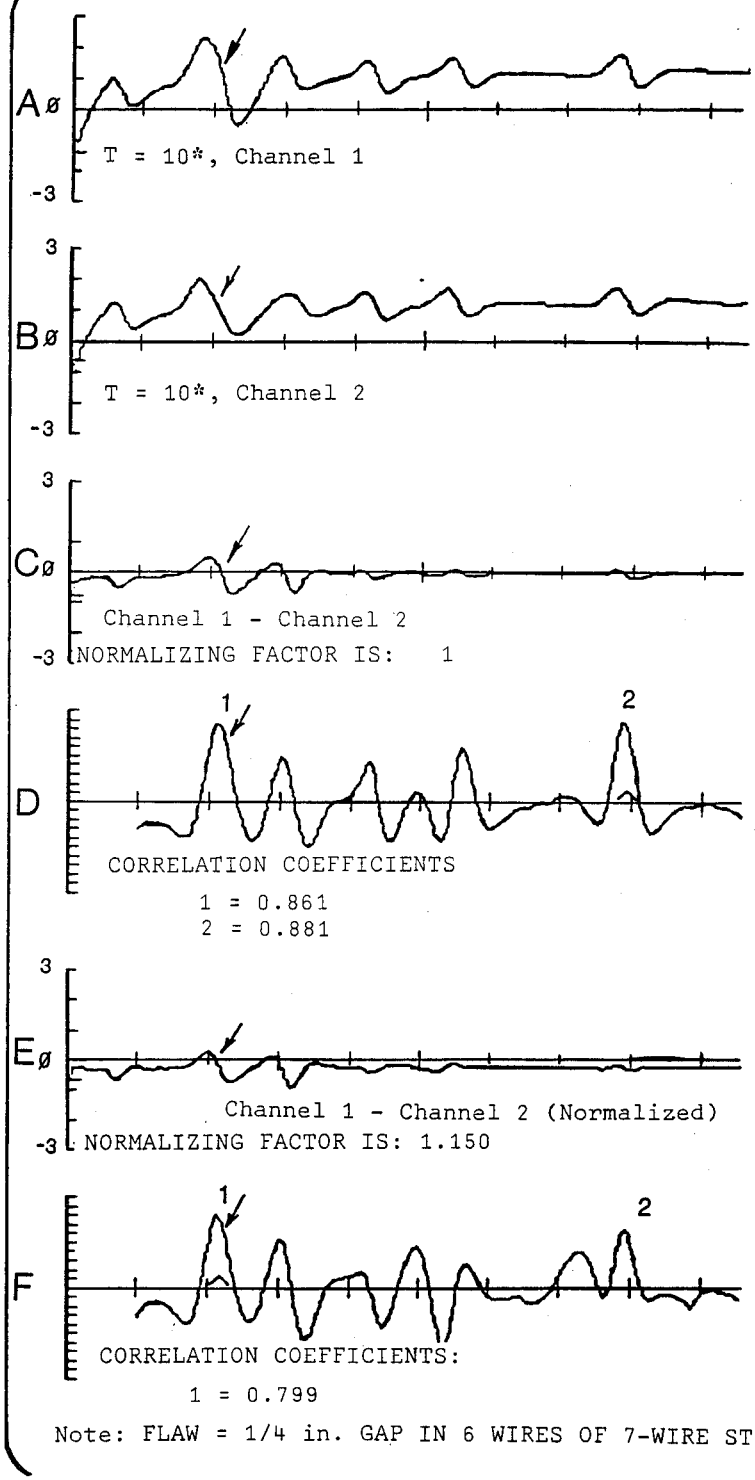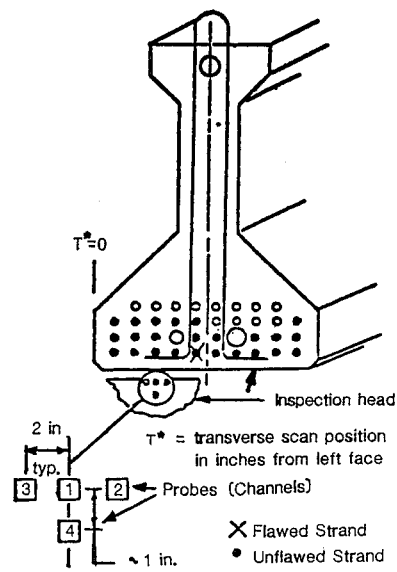
FIG. 10
Note: FLAW = 1/4 in. GAP IN 6 WIRES OF 7-WIRE STRAND

FIG. 11
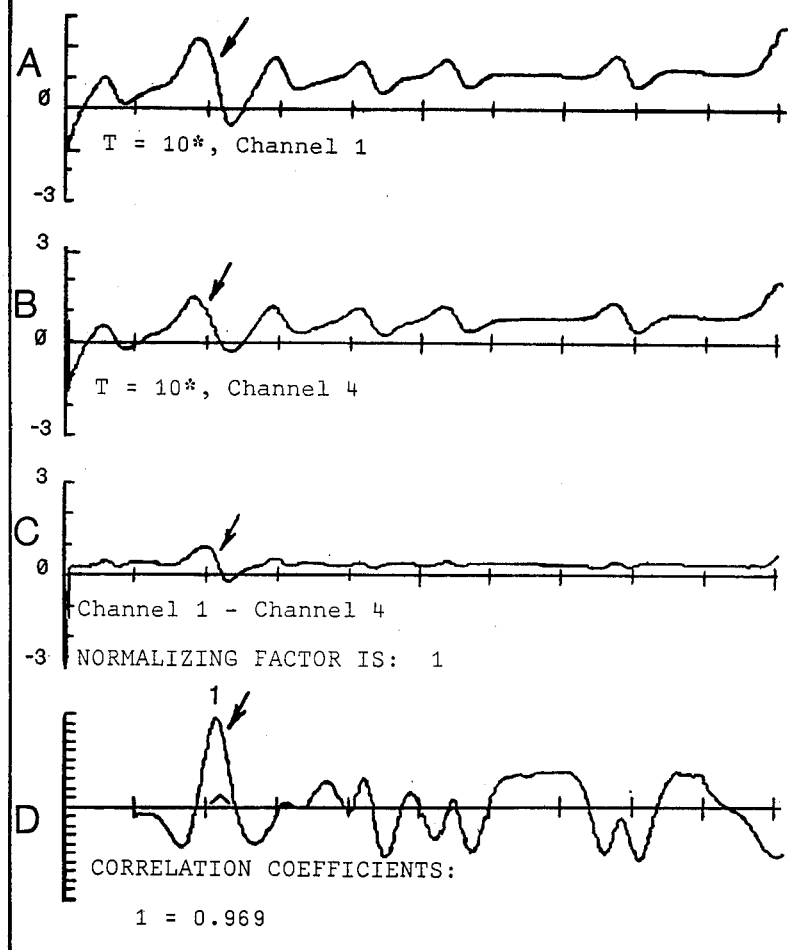
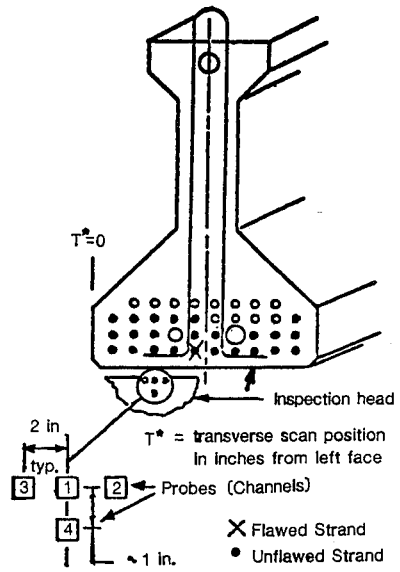
Note: FLAW = 1/4 in. GAP IN 6 WIRES OF 7-WIRE STRAND FIG. 14
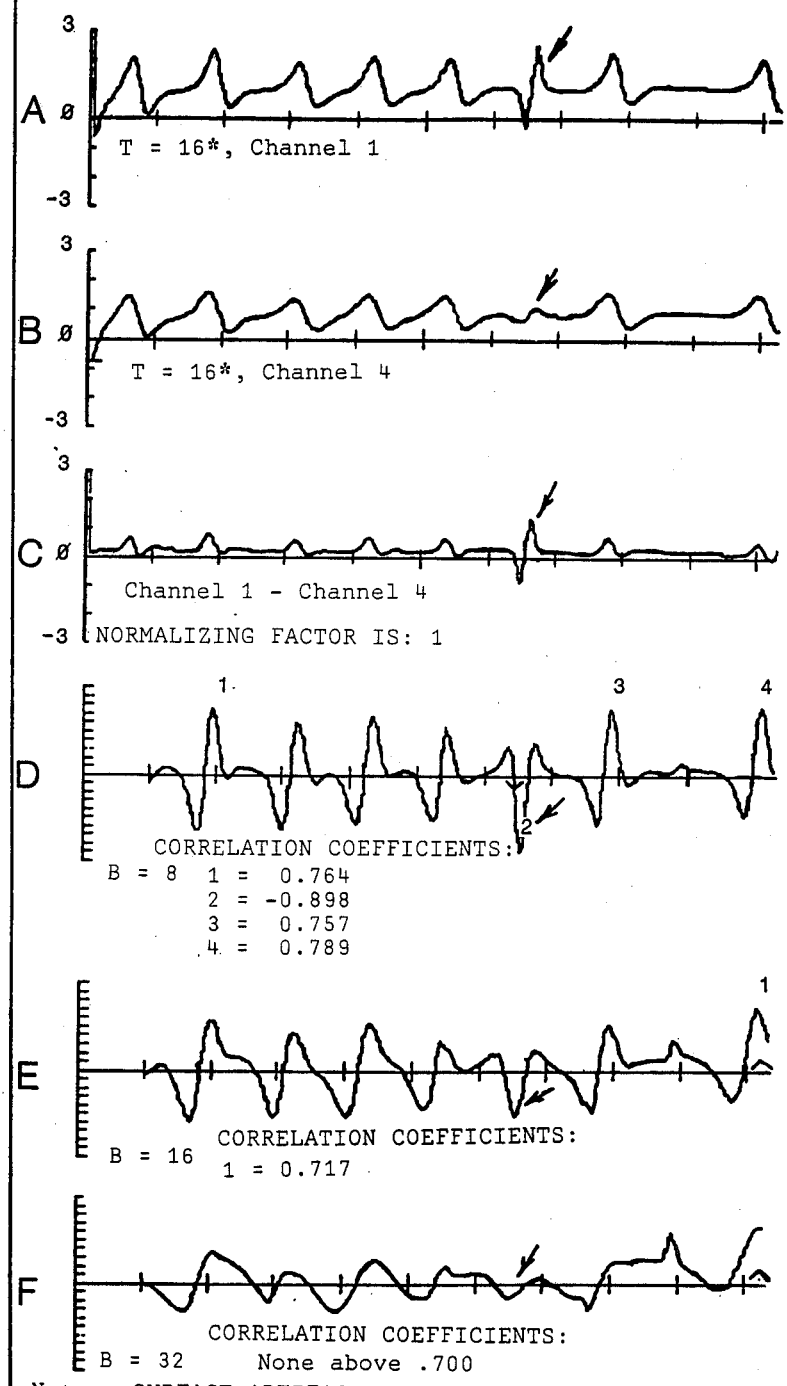
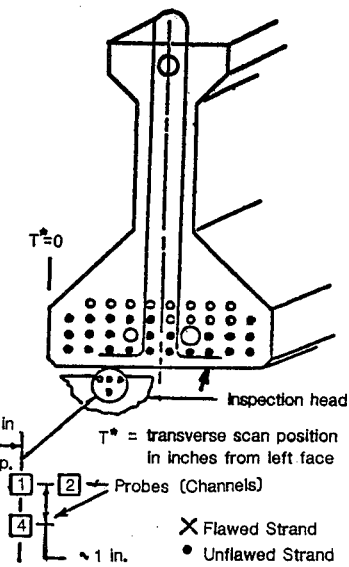

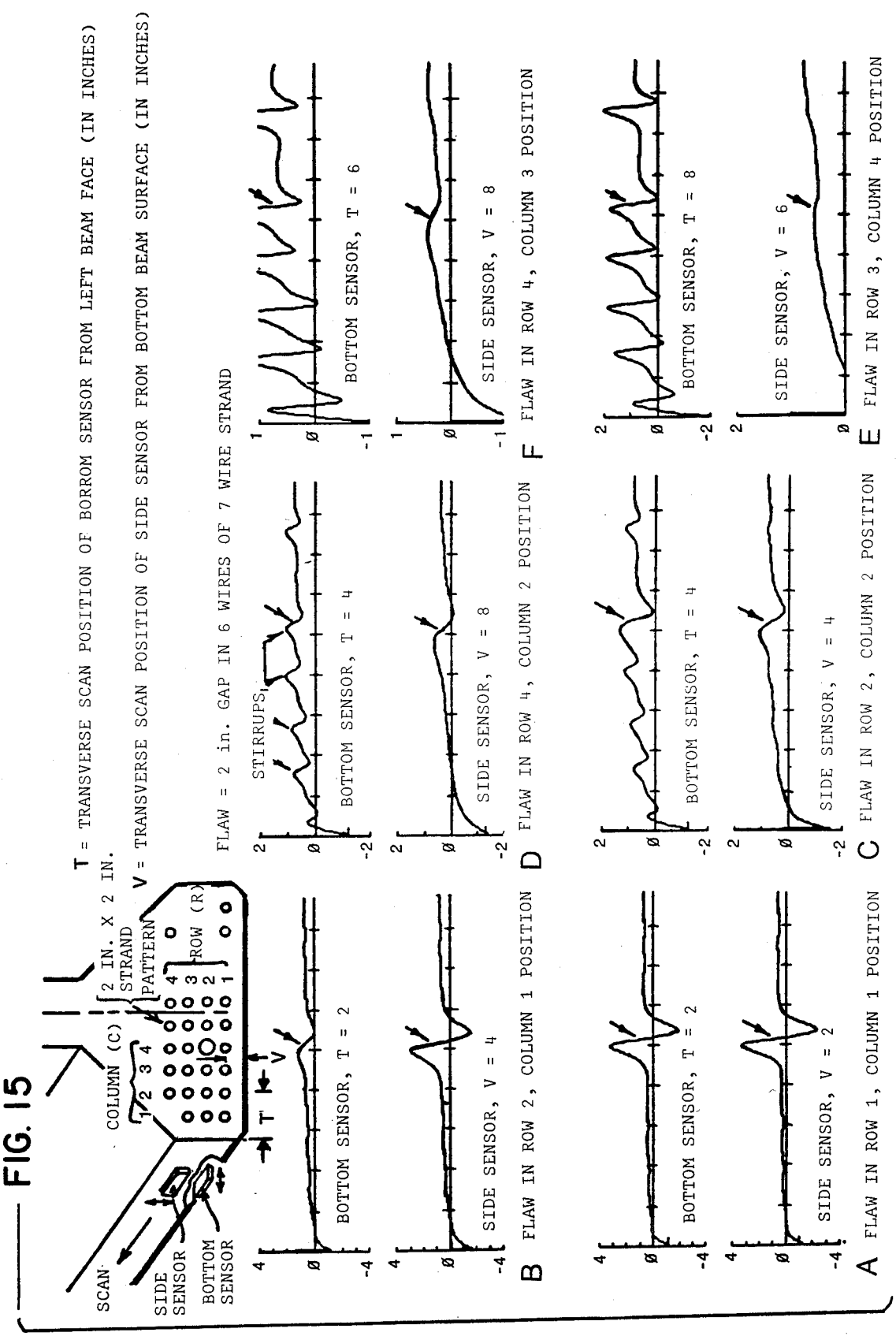

4,573,013

MAGNETIC INSPECTION OF REINFORCING STEEL RODS IN PRESTRESSED CONCRETE

STATEMENT OF GOVERNMENT INTEREST

The present invention was made under Government contract and may be made or used by or on behalf of the Government of the United States without the payment of any royalties thereon or therefor.

BACKGROUND

About 25 years ago, a new bridge structural design using prestressed concrete was introduced. In recent years, the use of prestressed concrete bridge beams has been widespread and such design now incorporates a variety of structural configurations. Prestressed concrete bridge structural members are of two general types, pretensioned and post-tensioned. Current pretensioned construction designs usually consist of 7-wire strands, on the order of ½-inch in diameter, arranged in a matrix on 2-inch centers and the strands are tensioned prior to pouring the concrete. Beams with pretensioned members are usually made at a plant site because of the special fabrication facilities and tooling required. In the case of the post-tensioned configuration, ducts, usually metal, are placed in a specified location and configuration before the cement is poured; subsequently, the reinforcing strand, rod, or bar is inserted and tensioned, usually at the bridge site, and grouting material is introduced to fill the space between the reinforcing member and the duct.

The load-carrying capability of prestressed bridge structural members is directly dependent upon the strength of the steel reinforcement rods, bars, or strands; hence, the integrity of this steel is of primary concern and is influenced by one or more of the following factors:

(1) Quality of manufactured reinforcement material—governed by dimensional tolerances, strength, ductility, metallurgical type flaws such as voids or impurities, and mechanical damage such as nicks, gouges, etc.
(2) Corrosion deterioration as a result of field environment.
(3) Fracture failure as a result of over-stress (caused by loss of section due to corrrosion deterioration) or by impact loading (as a result of construction or vehicular impact).
(4) Loss of bond between steel and concrete associated with corrosion of post-tensioned members due to voids in duct grouting collecting moisture.

In recent years, there is conclusive evidence that deterioration of the steel as a result of corrosion occurs; furthermore, such deterioration critically affects the structural strength. Currently used inspection procedures rely heavily on rust staining, cracking, and spalling of the concrete as an indicator that a problem exists in the reinforcing steel.

However, deterioration and even fracture of the reinforcing member can occur without being preceded by visual evidence on the external surfaces of the concrete members. For example, an elevated highway in a large city supported on 192 beams presently has more than 21 bars suspected of being fractured. Four such fractures have been confirmed. In this case, the presence of corroded and fractured post-tensioning bars was determined only from i) the projection of one end of the bars beyond the end of the beam during a visual inspection, ii) the loud noise made by one of the bars when it broke, which was heard by people in the area who reported it to the State, and iii) a broken bar which extended far beyond the end of the beam it was intended to reinforce, thereby interrupting traffic. There are no cracks or significant rust stains visible on the exterior surfaces of these particular beams.

From an overall point of view the problem is extremely broad because there is a wide variety of structural designs and the mechanisms contributing to the decrease or loss of structural integrity are complicated.

OBJECTS OF THE INVENTION

Accordingly, it is an object of the present invention to provide a method of inspecting the reinforcing members in prestressed concrete.

It is a further object to provide such a method which can be used on either pretensioned or post-tensioned members.

It is a further object to provide such a method which can detect partial as well as total failure of the member.

It is a further object to provide such a method which produces a printed record of the results of the inspection.

It is a further object to provide a method of enhancing the raw data from an inspection to eliminate the effects of reinforcing members not of interest.

BRIEF DESCRIPTION OF THE DRAWINGS

FIG. 3 shows the location of the reinforcing members in the test beam.

FIG. 4 shows the effect.of increasing fracture end separation in a 1⅜ inch diameter bar.

FIG. 5 shows the effect of different flaw sizes in a 1 inch diameter bar.

FIG. 6 shows the effect of different flaw sizes in a ½ inch diameter 7 wire strand.

FIG. 7 shows the effect of position within the strand matrix.

FIG. 8 shows the effect of a transverse reinforcing member at varying distances from a flaw.

FIG. 9 shows the signatures obtained at the end of a beam or scan.

FIG. 10 shows the results of data enhancement by the subtraction process.

FIG. 11 shows the results of data enchancement by the subtraction and correlation process.

FIG. 14 shows the signature of a piece of wire scrap near the bottom of the beam.

FIG. 15 shows a comparison between side mounted sensors and bottom mounted sensors.

SUMMARY

Briefly, the present invention is a method of magnetically inspecting a reinforcing member in prestressed concrete. A magnetic field is passed through the member and measured with an array of Hall effect sensors; anomalies in the field indicate the presence of flaws in the member. Methods of enhancing the raw data, by subtracting the data obtained from one sensor from that obtained from another sensor, to eliminate the effects of transverse reinforcing members are also shown.

DESCRIPTION OF THE PREFERRED EMBODIMENT

Figure 1:
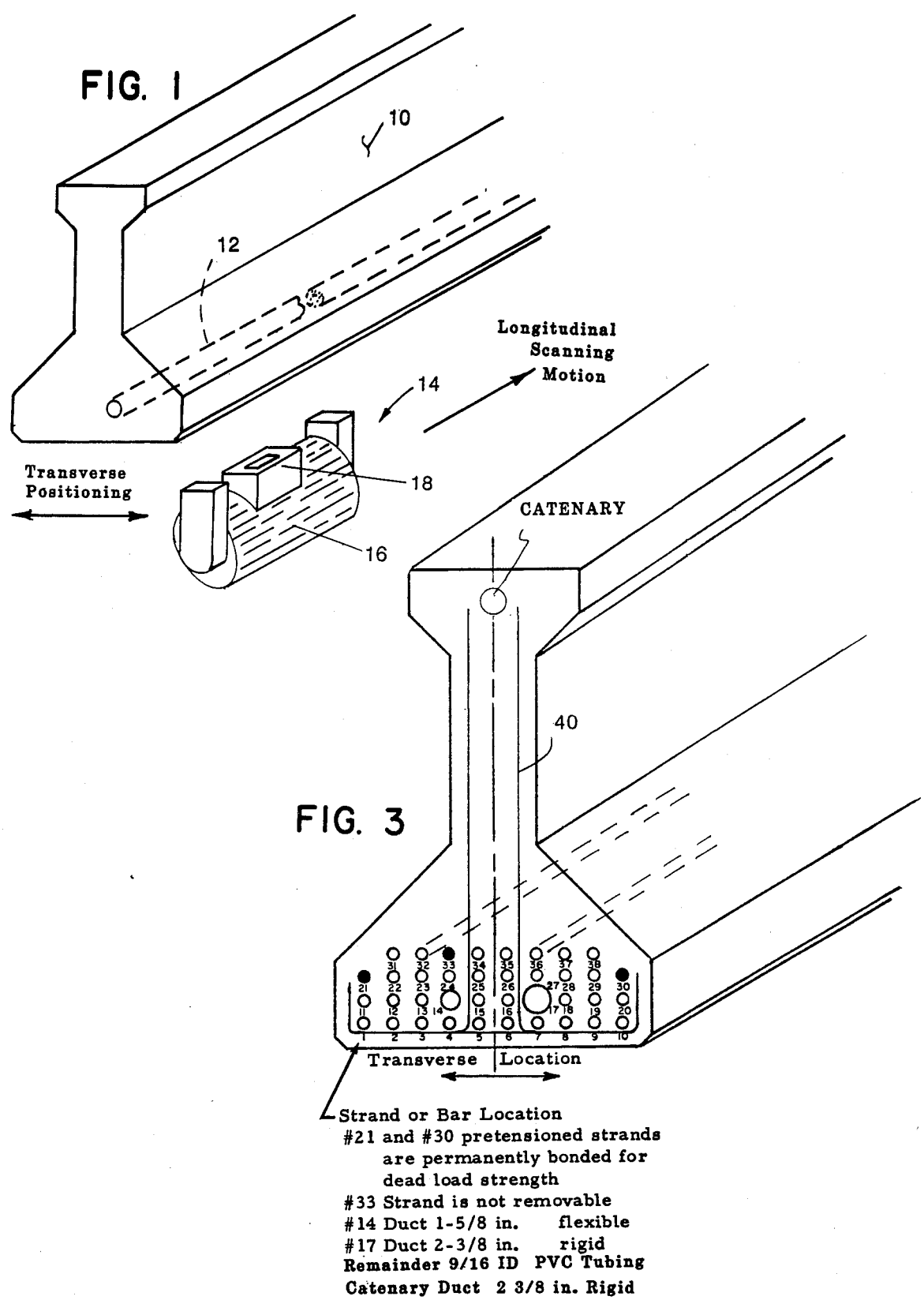
FIG. 1 shows an overall view of an inspection system of the present invention.

FIG. 1 shows an overall view of a prestressed concrete beam 10 having a fractured prestressing element 12 within it that is to be inspected by the magnetic field inspection system of the present invention. Electromagnet/sensor assembly 14, which comprises an electromagnet 16 and a Hall effect sensor 18 mounted between the pole pieces of electromagnet 16, is mounted on cart 20 (see FIG. 2) that rides on rails (not shown) which are suspended from beam 10.

Electromagnet 16 comprises 5700 turns of 14 gage aluminum magnet wire wound around a soft iron core. A current of 2 amps DC is put through it, producing 11,400 ampere-turns of magnetization. It is necessary to produce a magnetic field that extends to and is within all of the reinforcing members to be inspected, otherwise the members cannot be inspected. It is also necessary that the axis of electromagnet 16 be parallel to the members in order that the magnetic field be parallel to them rather than cut across them.

Hall effect sensor 18 is a model FH-301-040 sensor manufactured by F. W. Bell, Inc., 6120 Hanging Moss Road, Orlando, FL 32807.

Figure 2:
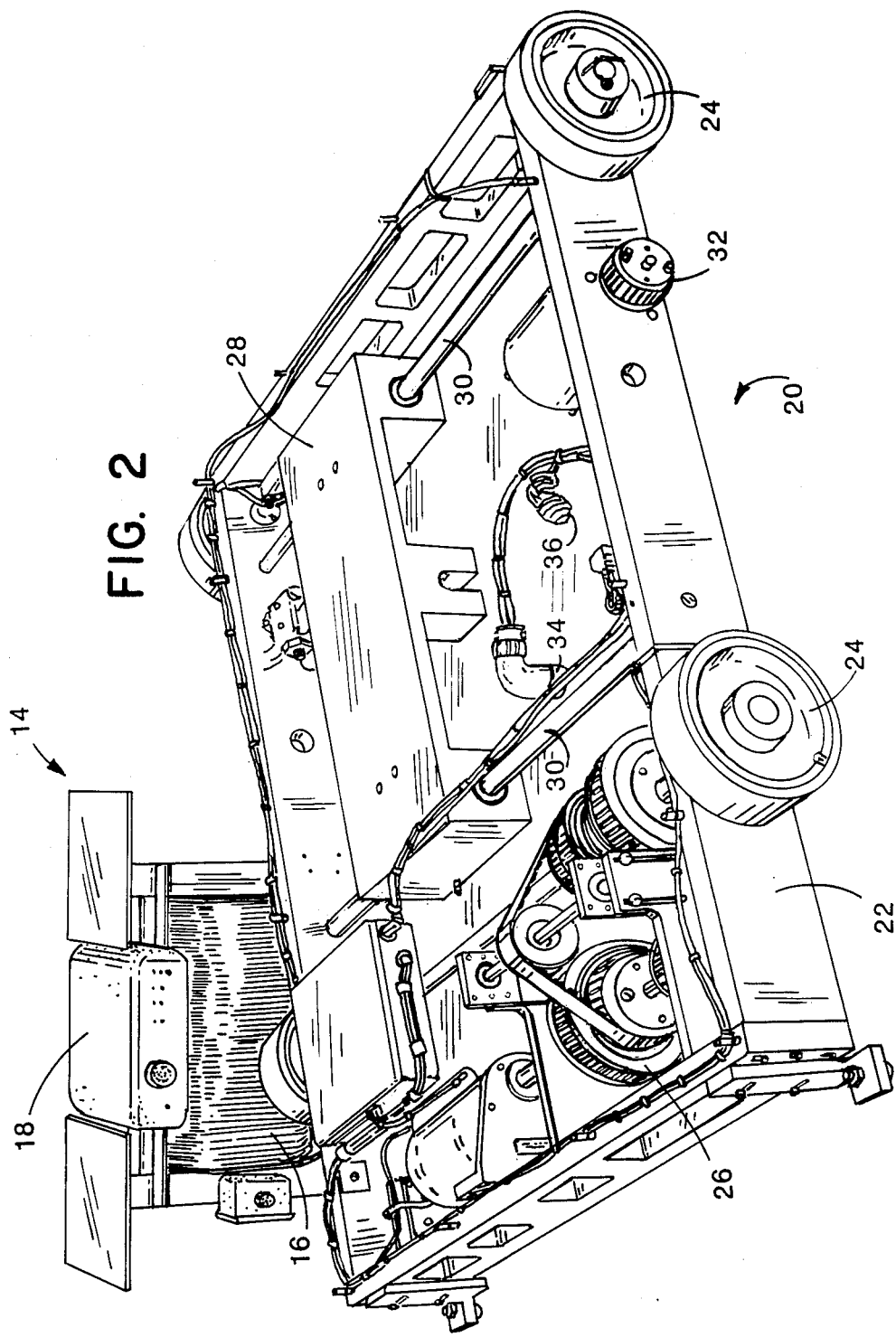
FIG. 2 shows the cart and sensor assemblies.

Cart 20 as shown in FIG. 2 comprises body 22 mounted on wheels 24 which are driven by longitudinal drive system 26. Within body 22 is magnet platform 28 which is mounted on guide rods 30; magnet platform 28 is moved transversely of body 22 on guide rods 30 by transverse drive system 32. Cart 20 must be made wide enough to allow electromagnet/sensor assembly 14 to be placed beneath the reinforcing members near the sides of the beam (members 1 and 10 in FIG. 3) in order to inspect all of the members. When the system is to be used to inspect a beam, electromagnet/sensor assembly 14 is mounted on magnet platform 28 and hooked up to the electrical system by connectors 34 and 36.

FIG. 3 shows the distribution of reinforcing members (rods or strands) within the test beam, which is a Texas Type "C" beam. There are 38 longitudinal members as well as stirrups 40 which are used to reinforce the web of the beam; there are many such stirrups along the length of the beam, but only one is shown. Of the longitudinal members, numbers 21, 30, and 33 are permanently bonded into the beam; number 14 is a $1\frac{3}{8}$ inch diameter flexible steel duct, number 17 is a $2\frac{3}{8}$ inch diameter rigid steel duct, and the rest are 9/16 inch inside diameter rigid PVC tubing. During testing a reinforcing member of known configuration (rod or strand, flawed or non-flawed) is put into one of these tubes or ducts and a magnetic "signature" of that member is recorded on a conventional strip chart recorder (not shown).

Operation of the inspection system is as follows. The rails which support cart 20 are suspended from the beam to be inspected by any means, or they can be supported from the ground; the only requirement is that they allow the cart to remain a constant distance from the underside of the beam. The distance between the rails and the beam is then adjusted to give the minimum practical gap between the top of electromagnet/sensor assembly 14 and the bottom of the beam being inspected. Cart 20 is then moved longitudinally under the beam and the output of the Hall effect sensor is recorded on the strip chart recorder. Since the output of the Hall effect sensor is a voltage that is proportional to the magnetic field that exists at the sensor and this field is influenced by the steel within the prestressed members, the output is an analog equivalent of the magnetic field.

At this point it should be pointed out that interpretation of inspection data from a beam is practically impossible without the aid of a construction drawing of the beam which shows the approximate location of all reinforcing members within the beam. As will be shown later, it was found that the signature of a stirrup or rebar chair (a small steel support used to hold a reinforcing member in place when the concrete is poured) is similar to that of a flaw. Another time a flaw-like signature was found whose location did not correspond to any reinforcing members or rebar chairs; upon closer inspection and partial excavation it was found to be caused by a scrap of the wire that was used to tie the reinforcing members together and which had not been removed from the form before concrete was poured. Without a construction drawing it would be difficult or impossible to determine if a signature were from a flaw or a transverse reinforcing member, unless the data enhancement techniques shown later are used.

FIG. 4 shows the signature response from a $1\frac{3}{8}$ inch diameter high-strength steel bar with a simulated fracture and varying degrees of separation between the fractured ends. The data shown in FIG. 4 are for the center line of the flawed bar 3.5 inches above the bottom surface of the test beam being scanned; the clearance between the magnet pole faces (and Hall effect sensor) and the concrete surface of the beam was approximately 0.5 inch. As can be seen, the record of the magnetic field is a straight line where there are no transverse reinforcing members or fractures in the prestressed members; where these exist they produce a signature which is an anomaly in the record in the form of a voltage spike or hump. Note that the signature from the simulated fracture for 0.5 inch separation and greater can be readily distinguished from those produced by the transverse stirrups. Furthermore, for the cases in which the simulated fracture is located between stirrups, end separations as small as 0.015 inches can be discerned because of the large horizontal extent of the signature. For record A at the top of FIG. 4, the horizontal distance between the upward-going and downward-going peaks of both the stirrup and fracture signatures has been indicated. This separation between the peaks is proportional to the distance between the sensor and the flaw and/or steel configuration causing the signature, and is a parameter which can be used to identify the depth of the element causing the signature. Note that the separation of the peaks for the stirrups is approximately one-third of that for the simulated fracture; correspondingly, the lower arm of the stirrups is approximately 1.5 inches from the bottom surface of the girder while the post-tensioned bar is approximately 3.5 inches from the bottom surface. This peak separation feature of the signatures will be referred to throughout since it is a parameter which can be extremely helpful in the interpretation of inspection results. A comparison of corresponding signatures in the four records of FIG. 4 shows excellent repeatability even though the bars were removed and replaced to set up the various flaw conditions. Also it is pointed out that stirrup signatures could be monitored to assess possible deterioration in the stirrup regions and to detect missing stirrups.

Signature responses from varying degrees of reduction in cross-sectional area (simulation of loss of section due to corrosion) for a 1 inch diameter high-strength steel bar are shown in FIG. 5. Record A shows the response from a 50-percent reduction in area over a ½ inch length in a 1 inch diameter bar; the insert shows a similar response from a slightly lower percentage reduction in area for a 1⅜ inch diameter bar. In all records of FIG. 5, the bar centerline is approximately 3.5 inches from the bottom surface of the concrete beam. Evaluation of the signatures for the 20-percent area reduction for this concrete coverage condition indicates a good probability for the detection of a 10-percent reduction in area provided adequate stirrup signature discrimination could be developed. Discrimination between configurational steel artifact signatures and simulated flaw signatures is discussed later.

FIGS. 6 and 7 present results from simulated flaws in a ½ inch diameter ×7-wire strand arranged in a typical 2 inch by 2 inch matrix. FIG. 6 presents results for varying degrees of strand deterioration with the flawed strand in the first row of the matrix (see partial cross-sectional view of the girder at the upper left corner). Inspection of records B and C indicates that detection of a 14 percent reduction in cross-sectional area would probably be marginal. The records in FIG. 7 show a rapid decrease in signature amplitude from the same size flaw for increasing depths of the flawed strand in the matrix Records B, C, and D of FIG. 7 present flaw signature data from an 86 percent reduction in area over a 2 inch length (removal of six wires from the 7-wire strand over a 2 inch length) with this flawed strand 2 inches, 4 inches, and 6 inches, respectively, above the bottom surface; unflawed strands adjacent to the flawed strand are present in all cases as indicated by the cross-section at the upper left in each record. The results in FIG. 7 indicate that detection of an 86 percent ×2 inch loss of section deeper than the first row of the matrix would probably be marginal.

The influence of signatures from reinforcement steel details, such as stirrups, holdowns, etc., on flaw signature recognition is illustrated in FIG. 8. Records B and C in this figure indicate that the field anomalies from the combined steel and flaw configurations are essentially cumulative. The combined effects can significantly modify the amplitude and shape of the resulting signal; for example, note the greater amplitude and significantly reduced horizontal separation between the upward-going and downward-going peaks (peak separation) of the combined stirrup and flaw signature in the record C of FIG. 8 as compared with that for the flaw signature only in the record A of the same figure. Importantly, the outstanding signature from the simulated fracture (0.5-inch separation) illustrated in FIG. 8 for a concrete coverage of approximately 3.5 inches indicates that such a condition should be readily detectable. However, the presence of other types of steel details as well as other complicating factors can significantly influence the interpretation of inspection data.

FIG. 9 shows records illustrating detection of deterioration (flaw condition) near the end of a beam which is resting on a bent such that an inspection scan to the end of the beam is not possible. The test beam was made so that the reinforcing steel configuration in end A was that of the end of the beam and end B was that of the middle of the beam; thus the results for end B simulate the results for the middle of a real beam. This was done because the catenary duct is much closer to the bottom of the beam at the middle than at the two ends and may have a greater effect on the magnetic field at the middle of the beam than at the two ends. The results in FIG. 9 indicate that the presence of a significant flaw (such as a bar fracture with 0.5 inch separation) can be detected even though the sensor cannot be placed directly beneath the flaw. Based on these results, it is estimated that a significant flaw can be detected when it is approximately 6 inches beyond the end of travel of the cart.

After a series of tests with multiple sensors arranged in transverse and vertical arrays it was found that the optimum configuration was an array of four sensors in two rows, with the first row comprising three sensors nearest the reinforcing members and the second row comprising one sensor below the middle sensor in the first row (see FIG. 10).

The entire array is between the pole pieces and the three sensors are flush with the pole pieces. Initially the horizontal and vertical spacing of the sensors was 1 inch; it was later found that a horizontal spacing of 2 inches provided better results. Obviously it would be possible to use just a single sensor and make 4 passes down the beam for each reinforcing member, with the sensor in a different location with respect to the magnet for each pass, but this is too time-consuming. In order to allow the data to be electronically enhanced and manipulated, it was magnetically recorded in addition to being displayed on the strip chart. For this purpose a shaft encoder assembly (not shown) was mounted on the inspection cart to provide spatial-interval sampling rather than time-interval sampling because the flaws are spatially distributed within the beam. Subsequent to data acquisition and storage, selected data were retrieved from mass storage and processed using several signal analysis routines. The results from various processing techniques were then compared to determine which approaches were most promising for the various types of flaw and steel artifact signal recognition and interpretation problems.

The different signal processing techniques that were explored are:

(i) Fast Fourier Transform (FFT)—a discrete Fourier transform applied using digital techniques to characterize the frequency spectra associated with a signal of interest. The thrust of this technique is to characterize the spectra associated with various signal types (stirrups, simulated flaws, artifacts, etc.) to determine if there are unique spectral characteristics associated with each.

(ii) Differencing,—point-by-point subtraction of signals from different scan tracks. The thrust of this technique is to enhance flaw signals with respect to those of stirrups and/or artifacts; and (iii) Correlation—a process similar to using a signal shape of interest as a template and sliding it along a scan record to determine if the template is a good match to any given region in the scan record. A good match between the template signal and a portion of the scan record indicates a high probability that the source of the template-type signal is present in the beam at a location corresponding to the matching location in the scan record. Mathematically, the correlation process quantitatively assesses the degree of shape matching between two signals. The correlation process is performed automatically by the logic unit under the command of the operator. The thrust of this technique is to quantitatively assess the degree of similarity between a selected signal or algorithm (mathematical representation of a flaw, a stirrup, an artifact or other type of signal) and those signals present in an unprocessed or previously processed scan record.

Combination of two or more signal processing techniques can provide powerful tools for signal enhancement and recognition. For example, a combination of differencing and correlation is very effective as will be shown later. Additionally, the use of knowledge about the steel configuration within the beam under inspection (from construction drawings) is very important in the application of any signal analysis method. The recognition of the symmetry or approximate symmetry of elements within the beam can provide guidance for selecting the specific differencing and correlation analyses. The recognition of certain types of elements from signal features in a set of scan data could provide great insight into the most fruitful analysis technique(s) to use.

Frequency spectra characterization of typical flaw signals and stirrups using the FFT approach showed little difference in response between these two types of signals. Furthermore, the results of correlation analysis, to be discussed later, have confirmed the similarity between stirrups and flaw signals. Accordingly, the bulk of the signal processing investigations were directed at the effective combination of the sensor array with differencing and correlation signal processing techniques. The added capability provided by use of a side sensor was also investigated. Typical examples of these techniques, along with the results obtained, are presented in FIGS. 10 and 11.

As explained above, differencing consists of the point-by-point digital subtraction of signatures from different channels and/or scan tracks. The object of this process is to enhance flaw signatures more than stirrup and/or artifact signatures through a prior knowledge of the steel configuration and/or symmetry. Signatures A and B in FIG. 10 show data acquired from Channels 1 and 2 by scanning a strand with a medium sized flaw, a ¼ inch gap in 6 wires of a 7-wire strand, for a strand position near the center of the beam (see sketch in FIG. 10 for strand location). The location of the flaw is indicated by the arrows in each signature. Record C in FIG. 10 shows the results of point-by-point subtraction of Channel 2 from Channel 1. Note, by comparison with the upper two signatures, that after differencing the stirrup signals are almost eliminated and the flaw signal is more recognizable. It is pointed out that in this differencing process, no adjustment of the signature amplitude for either channel was made; accordingly, the normalizing factor is equal to one.

Record E in FIG. 10 shows the result of subtracting Channel 2 from Channel 1 after multiplying Channel 2 by the normalization factor shown (records D and F will be reviewed after a brief discussion of the correlation process). The normalization factor was obtained from dividing the peak-to-peak amplitude of the fourth stirrup (reference stirrup) signal from the left in the Channel 1 record by the amplitude of the same stirrup signal in the Channel 2 signature. Note that the results of this normalization process are very similar to those obtained from an unnormalized, direct differencing of the two channels (previously shown by record C in FIG. 10).

Another example of the differencing process for the same strand location and flaw, previously presented in FIG. 10, is shown in FIG. 11. Signatures A and B in FIG. 11 were obtained from Channel 1 and Channel 4, respectively, for a scan directly beneath the flawed strand. In this case, the Channel 4 sensor element was located directly beneath the Channel 1 sensor element but 1 inch further beneath the beam. Accordingly, the signature should appear to be similar but somewhat reduced in amplitude. Record C presents the results of point-by-point subtraction of Channel 4 from Channel 1. In this case, note how much more outstanding the flaw signal is with respect to those from the stirrups.

In addition to the differencing approach, another powerful technique, mentioned earlier, is that of correlation analysis.

Correlation analysis is a mathematical process which quantitatively assesses the goodness of fit (or the degree of shape matching) between two signals or signatures. The quantifying number describing the fit is called the sample correlation coefficient, R. The correlation coefficient can be computed automatically, using the logic processing subsystem according to the following equation, where R is the sample correlation coefficient for signatures "a" and "b":

$$R = \frac{\sum\limits_{i}^{n} x_i y_i - n\overline{XY}}{\left[\left(\sum\limits_{i}^{n} x_i^2 - n\overline{X}^2 \sum\limits_{i}^{n} Y_i^2 - n\overline{Y}^2\right)\right]^{\frac{1}{2}}}$$

$x_i$ is the set of n data points describing the amplitude of the digital samples for signature "a" (i.e. the reference flaw)

$y_i$ is the set of n data points describing the amplitude of the digital samples for signature "b" (i.e. the suspected flaw)

$\overline{x}$ is the mean of the x data points $\overline{y}$ is the mean of the y data points n is the number of data points in each set The range of values possible for R is ±1. Correlation of two identically shaped signatures yields R = +1. Correlation of two signatures identical in shape but with reversed polarities yields R = +1. An important property of the correlation function above is that it is independent of the absolute amplitudes of the signatures being correlated.

The above correlation computation consists of the multiplication of two matrices, each matrix consisting of a set of numbers representing the location and amplitude of the digitized data points from a signal or signature. One axis in each matrix represents the location of each spatial sampling interval and the other axis represents the digital signal amplitude at each sampling interval. For the present application, a 101-point matrix representing a reference flaw signal was correlated against a 590-point matrix which represents an entire scan signature (such as record A in FIG. 10). The calculation is carried out by multiplying the 101-point matrix representing the reference flaw signal by the matrix representing the first 101 data points in the scan signature starting from the left, i.e. starting at data point 1 and extending through data point 101. Subsequently, the 101-point matrix representing the reference flaw signal is multiplied by the matrix representing the next 101 data points in the signature starting with data point 2 and extending through data point 102. This process is continued point by point along the scan signature and results in 490 correlation coefficients which are then plotted.

An example of a correlation coefficient plot is shown by record D in FIG. 10; this is based on record C, which is channel 1 minus channel 2. The greater the correlation coefficient value, the better the match between the flaw signal being used to interrogate the scan track and that segment of the scan signature which corresponds to the location of the correlation coefficient peak, and the higher the confidence that a flaw exists. The maximum correlation coefficient value in a correlation plot is indicated by the cursor (an inverted V) near the baseline pointing out the peak, such as that associated with peak 2 in record D of FIG. 10. The present processing program prints out the value of only those peaks greater than 0.700; however, any other value could be used.

In the case of record D, notice that the value of the correlation coefficient peak corresponding to the flaw location, 0.861, is slightly less than that of the maximum peak 2, 0.881, which corresponds to a stirrup. This would result in a stirrup being identified as a flaw, or would at best result in the identification of two possible flaws. To attempt to overcome this the normalizing factor was increased from 1.000 to 1.150 and the correlation coefficients were again calculated as shown in record F. The correlation coefficient peak associated with the flaw is the highest shown in the plot, but the value of peak 2 is sufficiently close to it to raise doubts.

As a final step the correlation coefficients were calculated for channel 1 minus channel 4, shown in FIG. 11. Record D clearly and unambiguously shows the flaw, with no other peaks as high as 0.700. Thus it is clear that the best flaw detection method is to use two sensors lined up directly beneath the member being inspected, subtract the output of the farther one from the output of the nearer one, and then calculate the correlation coefficients as shown.

Figure 12:
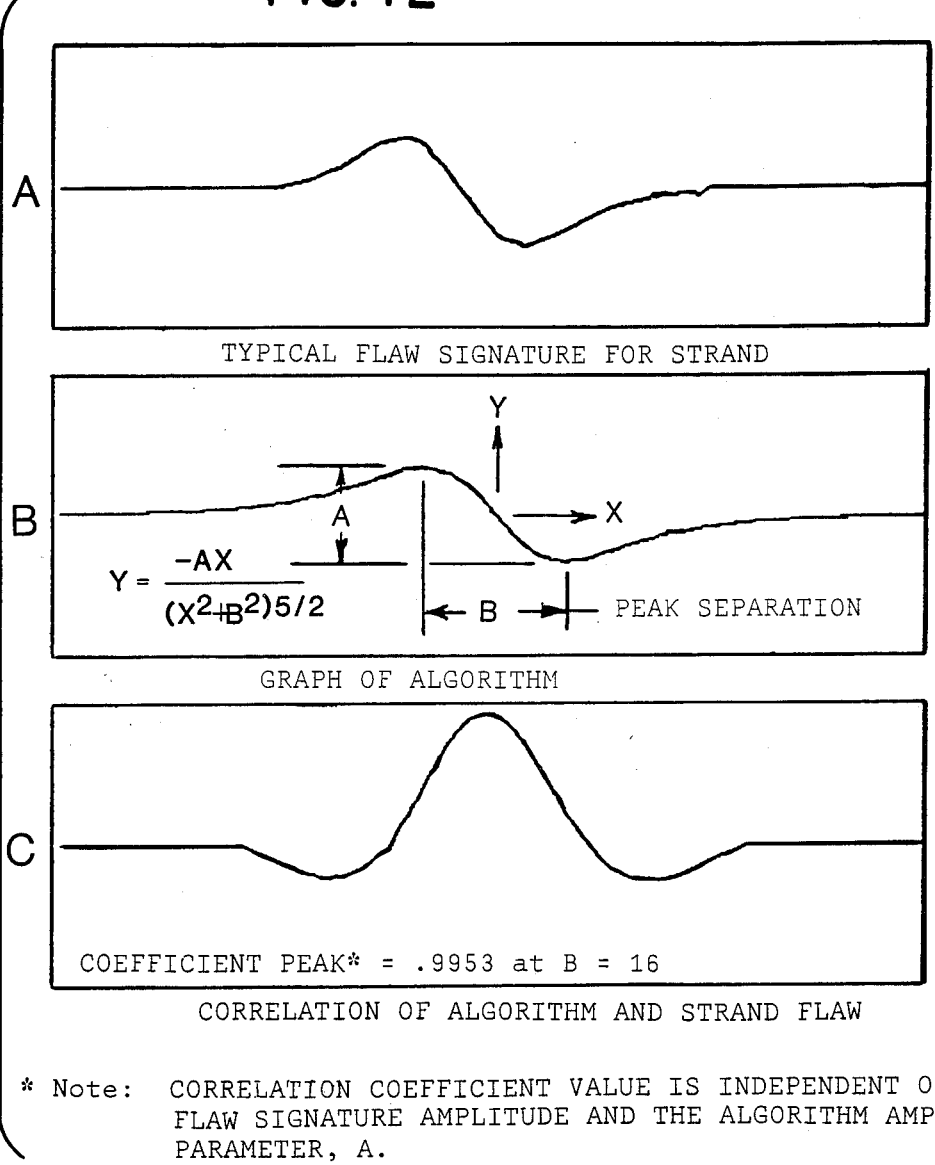
FIG. 12 shows a typical flaw signature, a flaw algorithm, and a correlation between the two.

Up to this point, a typical flaw signature has been considered for use as the interrogating correlation function. It is possible, however, to use an algorithm to represent the flaw signature and such a procedure facilitates modification of the flaw signal shape which can be shown to be related to certain flaw properties and to the depth of the flaw within the beam. FIG. 12 presents graphs of a typical signature, an algorithm (and its equation), and a plot of the correlation coefficient for the two signatures. The similarity between a graphical presentation of the algorithm equation and that of a typical flaw signature (from a ¼-inch gap in 6 wires of 7-wire strand) is obvious.

Figure 13:
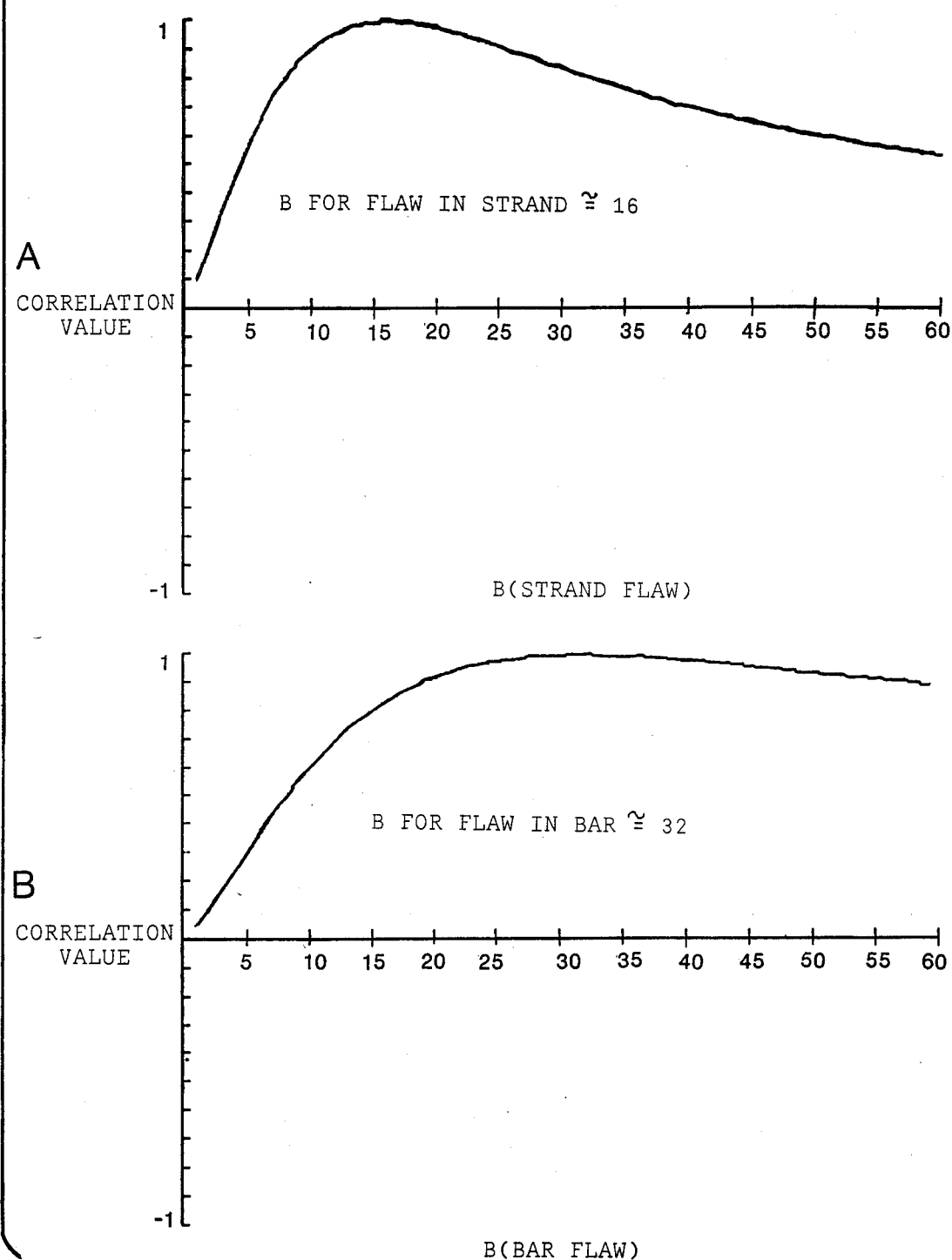
FIG. 13 shows correlation coefficients as a function of B.

The mathematical relationship for the algorithm in FIG. 12 was based on a theoretical model for the magnetic field perturbance from a sphere of permeability $u_o$ buried in an infinite volume of different permeability material, u. The two constants in the algorithm equation are A, which is related to amplitude, and B, which is a shape factor, usually referred to as peak separation. Peak separation is a parameter that is associated with the distance between the sensor and the flaw; the greater the sensor-flaw distance, the greater the value of B. The value of B may also be influenced by the length of the flaw if the distance over which the flaw extends is significant compared to the sensor-flaw spacing (e.g. extends over a distance equal to or greater than the sensor-to-flaw spacing). The goodness of fit between the algorithm and a typical flaw signature is confirmed in the fact that a maximum correlation value of 0.995 is obtained for a peak separation of B=16. All correlation results presented were obtained using the algorithm of FIG. 12; the value of B is indicated in each case. The graphs of correlation value as a function of B in FIG. 13 for typical flaws in a strand and in a bar were obtained by varying the B value of the algorithm when correlated against a flaw signal having a peak separation of B=16 for the strand flaw and B=32 for the bar flaw.

An important property of the correlation function, i.e. that inversion of polarity between the interrogating or flaw signal and a signal in the scan signature will result in a negative value of the correlation coefficient, makes it possible to eliminate the influence of disturbing elements such as wire scrap near the lower surface of the beam from further consideration. For example, records A and B in FIG. 14 show the influence of a 1½ inch long piece of 16 ga. iron "tie" wire on the magnetic signature from Channels 1 and 4 when scanned directly beneath the wire scrap. Because of the greater proximity of the wire scrap to the sensor of Channel 1 than to the sensor of Channel 4, the signal amplitude is greatly reduced on Channel 4 (see arrows in FIG. 14). In addition, notice that the signal from the wire scrap is inverted in polarity; that is, the wire signal is first downward-going then upward-going as viewed from left to right while the signal from a then upward-going as viewed from left to right while the signal from a stirrup is upward-going and then downward-going. Flaw signals have the same polarity as stirrup signals, upward-going then downward-going as viewed from left to right (see FIGS. 4–7 where the flaw signal is pointed out by the arrow). Record C in FIG. 14 shows the result of differencing Channel 1 and Channel 4—a prominent "opposite polarity" signal is obtained from the piece of wire mounted on the lower surface of the beam. Record D is a plot of the correlation coefficient for the differenced signature; note that the maximum coefficient (without regard for sign) corresponds to peak 2, from the wire scrap, but is negative in sign. It should be noted that this wire scrap correlation was obtained for B=8, indicating it is very near the lower surface of the beam. The lower two records in FIG. 14 show a progressively smaller value for the corresponding correlation peak (pointed out by the arrows) for values of B=16 and B=32. Accordingly, it is possible to discriminate between surface and near surface artifacts and flaws and those deeper within the beam; this can be done by merely varying the value of B in the correlation coefficient calculations to see which gives the greatest coefficient, the corresponding value of B providing the indication of depth (i.e. depth is proportional to the value of B).

A configuration wherein the sensor is placed against the side of the beam was also tried. FIG. 15 shows the results of this placement compared to those from placement against the bottom of the beam. In this comparison test, the magnet and sensor are aligned up directly below the column which contains the flawed strand, or the sensor is on the left side of the beam on the centerline of the row which contains the flawed strand and the magnet remains below the column which contains the flawed strand. When the flawed strand, is in the first row and first column as in records A the signals are approximately equal. When the flawed strand is moved to the column 1 row 2 position (records B), the side sensor produces a much clearer indication of the flaw since it is closer to the flawed strand than the bottom sensor. When the flawed strand is moved into the second, third, or fourth row (see records C, D, E, & F) the bottom sensor picks up the presence of the stirrups; the side sensor does not, since the stirrup is not between the sensor and the strand.

Note that the records shown in FIG. 15 are raw data; that is, they have not been differenced as in previous Figures nor have correlation coefficients been calculated for them. It is obvious that the use of two side sensors in the same horizontal plane, with the data manipulated as before, would produce equally clear results. In applications where there are substantial numbers of stirrups or other transverse reinforcing members, the use of side sensors may be preferable to the use of bottom sensors.

What is claimed is:

1. The method of inspecting the steel reinforcing members in prestressed concrete, said members being placed in a plurality of layers, each layer having a plurality of transversely spaced individual members, which comprises:

generating a magnetic field at a given transverse location across said prestressed concrete close enough to said reinforcing members that some of said magnetic field is within said reinforcing members;

obtaining an analog equivalent of said magnetic field at a given longitudinal location by means of a sensor placed in said magnetic field and recording said analog equivalent;

repeating the above steps at all points along the length of said members to produce a record of said magnetic field along the entire length of said members;

repeating the above steps at a different transverse location across said prestressed concrete; and inspecting said record to detect the presence of any anomalies in it, said anomalies providing an indication of the depth of the member as well as the presence of a flaw in the member.

* * * * *